United States Patent [19]

Kawakami et al.

[11] Patent Number: 4,899,009

[45] Date of Patent: Feb. 6, 1990

[54] METHOD FOR PRODUCING M-BENZYLTOLUNE

[75] Inventors: Shigenobu Kawakami, Ichikawa; Keiji Endo, Yokosuka; Hideyuki Dohi, Yokohama; Atsushi Sato, Tokyo, all of Japan

[73] Assignee: Nippon Petrochemicals Co. Ltd., Tokyo, Japan

[21] Appl. No.: 364,490

[22] Filed: Jun. 9, 1989

Related U.S. Application Data

[63] Continuation of Ser. No. 289,416, Dec. 21, 1988, abandoned, which is a continuation of Ser. No. 159,102, Feb. 23, 1988, abandoned.

[30] Foreign Application Priority Data

Sep. 9, 1987 [JP] Japan ................. 62-226214
Dec. 29, 1987 [JP] Japan ................. 62-332856

[51] Int. Cl.$^4$ ............................... C07C 5/22
[52] U.S. Cl. ......................... 585/471; 585/474; 585/475
[58] Field of Search ............... 585/471, 474, 475

[56] References Cited

U.S. PATENT DOCUMENTS

| Re. 29,857 | 12/1978 | Argauer . | |
|---|---|---|---|
| 2,282,327 | 5/1942 | Dreisbach | 260/668 |
| 2,308,415 | 1/1943 | Dreisbach | 260/668 |
| 3,702,886 | 11/1972 | Argauer | 423/328 |
| 3,714,021 | 1/1973 | Takahashi et al. | 208/232 |
| 3,753,188 | 8/1973 | Miyoshi et al. | 340/14 |
| 3,758,403 | 9/1973 | Rosinski | 208/120 |
| 3,786,107 | 1/1974 | Kuribayashi et al. | 260/672 T |
| 3,790,471 | 2/1974 | Argauer . | |
| 3,796,934 | 3/1974 | Munch | 317/259 |
| 3,926,782 | 12/1975 | Plank | 208/135 |
| 3,965,209 | 6/1976 | Butter | 260/671 |
| 4,011,274 | 3/1977 | Watanabe et al. | 260/668 |
| 4,035,285 | 7/1977 | Owen | 208/120 |
| 4,111,824 | 9/1978 | Schulz et al. | 585/25 |
| 4,111,825 | 9/1978 | Schulz et al. | 252/63 |
| 4,117,026 | 9/1978 | Haag | 260/671 |
| 4,228,024 | 10/1980 | Schulz et al. | 252/63 |
| 4,365,103 | 12/1982 | Chang et al. | 585/320 |
| 4,454,364 | 6/1984 | Farcasiu et al. | 585/470 |
| 4,463,209 | 7/1984 | Kursewicz et al. | 585/467 |
| 4,480,144 | 10/1984 | Smith | 585/481 |
| 4,523,044 | 6/1985 | Commandeur et al. | 585/11 |
| 4,642,730 | 2/1987 | Sato et al. | 585/471 |
| 4,686,548 | 8/1987 | Takashashi et al. | 503/225 |

FOREIGN PATENT DOCUMENTS

| 226152 | 6/1987 | European Pat. Off. . | |
|---|---|---|---|
| 3127905 | 2/1983 | Fed. Rep. of Germany | 5856.3/ |
| 62-55863 | 3/1987 | Japan . | |
| 1463359 | 2/1977 | United Kingdom . | |
| 1574523 | 9/1980 | United Kingdom . | |

OTHER PUBLICATIONS

Chem. Abstract No. 107: 236220a, p. 740 (1987).
Chen et al, "Industrial Application of Shape Selective Catalysis", *Catal. Rev.-Sci. Eng*, 28 (2&3), pp. 185-264 (1986).
Asakura et al, "Friedel-Crafts Isomerization of Phenyltolylmetehane and Ditolylmethane by Aluminum Chloride," Kinki Daigaku Kogakubu Kenkyu Hokoku, 1984, 18, 49-54.

*Primary Examiner*—Curtis R. Davis
*Attorney, Agent, or Firm*—Fisher, Christen & Sabol

[57] ABSTRACT

A method for producing m-benzyltoluene with a high yield and excellent selectivity without producing undesirable heavier by-products. The method is characterized in that toluene and diphenylmethane are allowed to react at a reaction temperature in the range of 170° to 400° C. in the presence of a crystalline synthetic zeolite catalyst in which the molar ratio of $SiO_2/Al_2O_3$ is 20 or higher and the openings of main pores are formed by ten-membered oxygen rings.

5 Claims, No Drawings

METHOD FOR PRODUCING M-BENZYLTOLUENE

This application is a continuation of prior U.S. application Ser. No. 289,416, filed Dec. 12, 1988 which is a continuation of application Ser. No. 159,102, filed Feb. 23, 1988, both now abandoned.

BACKGROUND OF THE INVENTION (1) Field of the Invention

This invention relates to a method for producing m-benzyltoluene. More particularly, the invention relates to the method for producing m-benzyltoluene with a high yield and good selectivity without producing undesirable heavier by-products.

(2) Description of Prior Art

There are three kinds of isomers of benzyltoluenes. The melting points of these three kinds of isomers are: p-isomer: 4.6° C.; o-isomer: 6.6° C.; and m-isomer: −27.8° C. That is, the melting point of the m-isomer is extremely low. Incidentally, materials having lower melting points are preferred, for example, in the field of heat transfer medium or the like because of the easiness in starting machines and other advantages. Accordingly, the m-isomer is most desirable among the benzyltoluene isomers in view of low temperature characteristics.

As the method for producing benzyltoluene, it has been a principal method in the conventional art that a halide such as benzyl chloride is reacted with toluene (U.S. Pat. No. 4,523,044 and European Patent Publication No. 226,152). Meanwhile, for the method of disproportionation of diphenylmethane and toluene like the present invention, only the use of aluminum chloride has been proposed.

In addition, in another method which has already been proposed by the present inventors, benzyltoluene is prepared from toluene and diphenylmethane in the presence of disproportionation catalysts of a solid acid such as silicaalumina or a Lewis acid such as aluminum chloride (Japanese Patent Application No. 62-55863). In the case, however, that aluminum chloride is used as a catalyst, much heavier products and by-products such as ditolylmethane are formed and the yield of benzyltoluenes is not always good. The selectivity to m-benzyltoluene is also low. Furthermore, when a solid acid catalyst such as silica-alumina is used, the reaction also leads to similar results.

As the crystalline synthetic aluminosilicate zeolite, there are known several zeolites such as mordenite and Y-type zeolite. Nevertheless, it was found by the inventors of the present application that these conventional zeolites are not suitable for use in the method of this invention because they are short in catalytic life, in other words, the lowering of catalytic activity is severe and the shape-selectivity is low.

So many applications of so-called ZSM-5 family zeolites are reported by N. Y. Chen, et al. (CATAL. Rev. SCI. Eng., 28(2&3), 185-264 (1986)). Such a production method of m-benzyltoluene, however, has not been known.

Accordingly, it has been looked for to propose a novel method for producing m-benzyltoluene with a good yield and a high selectivity.

BRIEF SUMMARY OF THE INVENTION

It is, therefore, a primary object of the present invention to provide an improved method for producing m-benzyltoluene which is free from the above-mentioned conventional disadvantages.

Another object of the present invention is to provide an improved method for producing m-benzyltoluene with excellent yield and selectivity.

In accordance with the present invention, the method for producing m-benzyltoluene is characterized in that toluene and diphenylmethane are allowed to react at a reaction temperature in the range of 170 to 400° C. in the presence of a crystalline synthetic zeolite catalyst which has a molar ratio of $SiO_2/Al_2O_3$ of 20 or higher and openings of main pores being formed by ten-membered oxygen rings.

DETAILED DESCRIPTION OF THE INVENTION

The present invention will be described in more detail.

The typical examples of the crystalline synthetic zeolite catalysts which have a molar ratio of $SiO_2/Al_2O_3$ of 20 or higher and openings of main pores being formed by ten-membered oxygen rings, are ZSM-5 type catalysts. By using such catalysts, m-benzyltoluene can be obtained at higher yield and higher selectivity as compared with the case of commonly used catalysts.

Incidentally, the method of xylene preparation by the disproportionation between toluene molecules in the presence of a ZSM-5 type zeolite, has already been disclosed (British Patent No. 1,463,359). This reaction is attained by the transferring of methyl groups, as a matter of course.

If the transfer of methyl groups is caused to occur in the preparation of benzyltoluene from toluene and diphenylmethane in the presence of ZSM-5 type zeolite, it is naturally presumed that xylene is produced because of the existence of toluene. If xylene is produced, the starting material is consumed that much to reduce the yield of benzyltoluene, which is not desirable. It is, therefore, presumed that the ZSM-5 type catalyst is not suitable for producing benzyltoluene from toluene and diphenylmethane.

Contrary to the above presumption, the present inventors have found a fact that benzyltoluene can be produced by causing the reaction to proceed without any substantial formation of xylene in spite of the existence of toluene. In addition, the selectivity to m-benzyltoluene is very high and o-benzyltoluene is not produced, substantially. That is, among three position isomers of benzyltoluenes, m-benzyltoluene is produced much.

For example, in the case that xylene is produced by disproportionating toluene in the presence of a catalyst of ZSM-5 and the ZSM-5 type zeolite is employed as it stands as a catalyst, the selectivity to p-xylene is hardly exhibited and the obtained xylene mixture has an equilibrium composition. For this reason, it has been proposed to modify ZSM-5 type zeolite with several metals (British Patent No. 1,574,523). However, according to the method of the present invention, much isomer (m-benzyltoluene) can be obtained without the necessity of any modification treatment.

Accordingly, it is quite a surprising fact that m-benzyltoluene can be produced much with producing substantially no xylene in the method of the present invention and this fact cannot be presumed from the foregoing patent publications.

In accordance with the method of the present invention, the reaction conditions between toluene and diphenylmethane are as follows:

First of all, the catalyst used in the method of the present invention is crystalline synthetic aluminosilicate zeolite or the like in which the molar ratio of $SiO_2/Al_2O_3$ is 20 or higher and the openings of main pores are formed by ten-membered oxygen rings. Exemplified as such zeolites are ZSM-5 type synthetic zeolites, zeolite zeta 1, and zeolite zeta 2 which have openings of main pores being formed by ten-membered oxygen rings. In other words, the zeolites used in the present invention is characterized by the ten-membered oxygen rings. The conventional synthetic zeolite of A type zeolite, erionite and offretite are smaller pore zeolites having eight-membered oxygen rings; and mordenite, X type zeolite and Y type zeolite are larger pore zeolites having twelve-membered oxygen rings.

These zeolites having eight-membered oxygen rings or twelve-membered oxygen rings are not suitable for use in the method of the present invention because the structures of them are quite different from the catalysts used in the present invention.

Provided that crystalline synthetic aluminosilicates have the characteristic structure of the openings of main pores being formed by ten-membered oxygen rings and have a molar ratio of $SiO_2/Al_2O_3$ of 20 or higher, any of crystalline synthetic zeolites can be used in the method of the present invention. Preferable catalysts among them are ZSM-5 type synthetic zeolites which are known as ZSM-5, ZSM-11, ZSM-12, ZSM-22, ZSM-23, ZSM-35, ZSM-38, and ZSM-48. Any of these ZSM-5 type synthetic zeolites have the characteristic structure of the openings of main pores being formed by ten-membered oxygen rings. Especially preferable synthetic zeolite is ZSM-5. The compositions and preparation methods for these ZSM-5 type zeolites are disclosed in the following patent publications.

ZSM-5: U.S. Pat. No. 3,702,886
ZSM-11: U.S. Pat. No. 3,709,979
ZSM-22: U.S. Pat. No. 4,481,177
ZSM-23: U.S. Pat. No. 4,076,842
ZSM-23: U.S. Pat. No. 4,490,342
ZSM-35: U.S. Pat. No. 4,016,242
ZSM-38: U.S. Pat. No. 4,045,859
ZSM-48: U.S. Pat. No. 4,423,021
Zeolite Zeta 1: Japanese Laid-Open Patent Publication No. 51-67299
Zeolite Zeta 2: Japanese Laid-Open Patent Publication No. 51-67298

The synthetic zeolites having the openings of main pores that are formed by ten membered oxygen rings, generally have very high molar ratios of $SiO_2/Al_2O_3$. The values are generally not lower than 20. In some case, the molar ratio of $SiO_2/Al_2O_3$ is very high to reach 1600 or higher, which is also effective in the method of the present invention. In addition, it is also possible to use the zeolite having an $SiO_2/Al_2O_3$ molar ratio of almost infinity which contains substantially no aluminum such as silicalite. The "high-silica" zeolite like this is also covered in the definition of the present invention. This $SiO_2/Al_2O_3$ molar ratio are determined by an ordinary analysis method such as atomic absorption analysis. This molar ratio represents a value as close as possible to the ratio in the hard anion skeleton in zeolite crystals excluding the aluminum in cations or in other forms in binders or channels.

The structure of the ten-membered oxygen rings of the openings of pores are generally confirmed by X-ray diffractiometry. For example, the ZSM-5 type synthetic zeolites which are preferably used in the present invention, have characteristic X-ray diffraction patterns, respectively (cf. the foregoing patent publications).

Meanwhile, in place of this X-ray diffractiometry, values of constraint index can also be employed. That is, the constraint indexes of the ten-membered oxygen rings of the zeolite in the present invention are defined to be 1 to 12. The practical method to determine the constraint index is described in U.S. Pat. No. 4,288,647. This constraint index indicates the degree that fine pore structure of zeolite crystals control the access of molecules having cross-sectional areas larger than that of n-paraffin. As described in the above patent gazette, n-hexane and 3-methylpentane are adsorbed by zeolite under certain conditions and the value is calculated from the quantity of adsorption. Typical values of constraint indexes are as follows:

| Catalyst | Constraint Index |
| --- | --- |
| ZSM-5 | 8.3 |
| ZSM-11 | 8.7 |
| ZSM-35 | 4.5 |
| Amorphous silica-alumina | 0.6 |

The method for synthesizing the zeolite that is used in the present invention will be described taking an example of ZSM-5. In the first place, a reaction mixture of tetrapropyl ammonium hydroxide, sodium oxide, aluminum oxide, silicon oxide and water is prepared. The composition of the mixture is made within the range as described in the foregoing patent gazette. This reaction mixture is then heated to cause hydrothermal synthesis. After the synthesis, the obtained crystals are baked in the air to obtain zeolite ZSM-5 catalyst. The tetrapropyl ammonium hydroxide can be synthesized in situ from n-propylamine and n-propyl bromide in the reaction system. The method using aluminum oxide was described herein, however, a preparation of ZSM-5 containing substantially no aluminum is also proposed. Tetrapropyl ammonium hydroxide is used in the above method. It is also proposed, however, to use several organic cations or other organic compounds as precursors besides the above compound. Exemplified as these compounds are ammonia, trialkylmethylammonium cations, triethyl-n-propylammonium cation, $C_2$ to $C_9$ primary monoalkylamines, neopentylamine, di- or trialkylamines, alkanolamines, $C_5$ to $C_6$ alkyldiamines, $C_3$ to $C_{12}$ alkylenediamines, ethylenediamine, hexamethylenediamine, $C_3$ to $C_6$ diols, ethylene or propylene glycol, pentaerythritol, dipentaerythritol, tripentaerythritol, 1,4-dimethoxycyclohexane, hydroquinone, ethylene oxide and ammonia, n-dodecylbenzene sulfonate, cyclopentadienyl phthalocyanine complex, 2-aminopyridine, ethylene glycol dimethyl ether, dioxane, dioxolan, and tetrahydrofuran, aliphatic carboxylic acids such as tartaric acid. Furthermore, even it is also proposed to add ZSM-5 as the seeds for crystallization without adding the above exemplified organic cations or organic compounds as precursors thereof.

Owing to the composition of the reaction mixture for synthesis of catalyst, the zeolite used for the reaction of the present invention contains metal ions such as sodium ions or other metal ions. Those ion-exchanged with other metals of alkaline earth metals such as calcium and magnesium, and trivalent metal ions such as rhenium and cerium, can be used. Furthermore, it is possible to use crystalline synthetic aluminosilicate zeolites such as ZSM-5 type zeolites that are modified by boron, potassium, phosphorus or their compounds can also be used. These ion-exchange or modification can be carried out according to conventional art.

As described above, the crystalline synthetic zeolite in the present invention can contain various kinds of metals. However, the hydrogen type zeolite which are made by exchanging the metal ions with hydrogen ions are preferable for the method of the present invention. A typical hydrogen type zeolite can be prepared by steps such that the catalyst containing organic cations during the catalyst preparation is heated in an inert atmosphere, for example, at 400 to 700° C. for 1 hour, after that, ion exchange is done with an ammonium salt or mineral acids such as hydrochloric acid, which is followed by baking at 300 to 600° C. to activate.

The reaction temperature in the method of the present invention is in the range of 170 to 400° C. and more preferably 200 to 350° C.

When the reaction temperature is lower than this range, the conversion rate of starting materials is low. On the contrary, if the reaction temperature is higher than this range, by-product of xylene or the like is produced. Accordingly, they are not desirable.

The reaction can be carried out in the vapor phase, however, the liquid-phase reaction is more desirable for maintaining the catalytic activity. Furthermore, the reaction in the vapor phase inevitably requires a high reaction temperature and, as described above, the side reaction to produce xylene is caused to occur at higher temperatures. Therefore, the reaction is carried out in the liquid phase.

In order to carry out the reaction in the liquid phase, it is desirable that the reaction pressure is set to a value which is suitable for maintaining the reaction phase in liquid. This pressure is generally selected from a range of the atmospheric pressure to 50 kg/cm$^2$.

The type of reaction in the method of the present invention may be any of continuous system and batch wise system. In the batch wise system, the reaction time is selected from the range of 0.5 to 50 hours in accordance with reaction temperatures and other reaction conditions. When the reaction time is shorter than this range, the rate of conversion is low. On the other hand, even when the reaction time is excessively prolonged, the yield of benzyltoluene can be improved no more and it rather results in the occurrence of undesirable side reaction.

In the case of continuous reaction system, the value of LHSV (liquid hourly space velocity) is in the range of 0.2 to 20, preferably 0.5 to 10. When the LHSV is smaller than the above range, much side reaction is caused to occur and the yield per unit time length is lowered. Accordingly, it is not desirable. On the other hand, when the LHSV is excessively large, it is also undesirable because the reaction cannot proceed well and much unreacted materials are discharged from the system.

In the batch wise system, 0.1 to 10%, preferably 0.5 to 5%, by weight of catalyst relative to the weight of reaction mixture may be used. When the concentration of the catalyst is lower than this range, the reaction cannot proceed well. On the other hand, even when the concentration of catalyst is raised above that range, the yield of the intended product is not always improved, so that it is wasteful to use too much catalyst.

The molar ratio of toluene to diphenylmethane to be fed to the reaction system is in the range of 0.5 to 20 and preferably 1 to 10. When the molar ratio is lower than this range, that is, the quantity of toluene is too small relative to the quantity of diphenylmethane, the conversion rate of materials is undesirably lowered. On the other hand, when the molar ratio of toluene is too high using excessive quantity of toluene as compared with the above desirable range, the obtainable quantity of benzyltoluene per one reaction operation is small, which is not desirable.

After the reaction, unreacted toluene, diphenyl methane and benzene and ditolylmethane which are by-product of the disproportionation of the present invention, are separated from the reaction mixture to obtain the m-benzyltoluene of the present invention.

It should be noted that the heavier products are not produced by side reaction in the method of the present invention as compared with the conventional method to use aluminum chloride catalyst. This advantage can be obtained likewise when compared with the case of silica-alumina catalyst. In addition, the formation of o-benzyltoluene is not caused to occur substantially in the present invention and m-benzyltoluene can be prepared with excellent selectivity and yield.

In the following, the method of the present invention will be described in more detail with reference to several examples.

Catalyst Preparation Example

According to Example 2 of British Patent No. 1,402,981, aluminum sulfate, sulfuric acid, tetra-n-propylammonium bromide, water glass and water were blended with stirring to prepare homogeneous gel-like slurry. After the crystallization with stirring at 160° C. for 72 hours in an autoclave, water rinsing and filtration were repeated until the rinse filtrate became neutral, thereby obtaining zeolite ZSM-5 of 70 in $SiO_2/Al_2O_3$ molar ratio. The obtained zeolite was baked in the air to prepare a catalyst. The X-ray diffraction chart of this catalyst agreed with that of the foregoing U.S. Pat. No. 3,702,886. In addition, the value of the above-mentioned constraint index was also consistent with the value of the above gazette. Therefore, it was understood that the catalyst have the structure characteristic that the openings of main pores formed by ten-membered oxygen rings.

EXAMPLE

The zeolite ZSM-5 prepared in the above Catalyst Preparation Example was subjected to ion exchange with hydrochloric acid to obtain a 200 ml hydrogen type ZSM-5 (12 to 14 mesh). This was fed into a 250 ml reaction vessel and was dried for 3 hours at 480° C. with a feed of dry nitrogen gas.

A liquid mixture of 2 moles of toluene and 1 mole of diphenylmethane was fed to the reaction vessel at a reaction temperature of 270° C., a pressure of 20 atm. (under nitrogen atmosphere) and LHSV of 1.0.

The effluent reaction mixtures were analyzed by gas chromatography to determine the compositions after certain hours' reaction. The results of them are shown in the following Table 1.

COMPARATIVE EXAMPLE 1

A 200 ml reaction vessel was filled with 200 ml of a solid acid catalyst, silica-alumina catalyst N-632L (trademark, made by JGC Corp., particle size: 12-14 mesh) and the catalyst was dried at 250° C. for 24 hours by a feed of dried nitrogen. A liquid mixture of 2 moles of toluene and 1 mole of diphenylmethane was fed to the reaction vessel at a reaction temperature of 270° C., a pressure of 20 atm. (under nitrogen atmosphere), and LHSV of 1.0. The reaction mixtures were analyzed by gas chromatography in the like manner as in Example to determine the compositions after certain hours' reaction. The results of them are shown in the following Table 2.

According to the results in Table 1 and 2, it was understood that the selectivity to benzyltoluene of ZSM-5 catalyst is higher as compared with the use of the silicaalumina catalyst and that the selectivity to m-benzyltoluene among the benzyltoluenes is also high. Furthermore, it is understood that the rate of the reduction of catalytic activity of ZSM-5 catalyst is smaller.

COMPARATIVE EXAMPLE 2

To a 1 liter separable flask were fed 4 moles of toluene, 2 moles of diphenylmethane and 10 g of aluminum chloride catalyst. The contents were stirred for 5 hours at room temperature. After that, the catalyst was deactivated and the reacted mixture was analyzed in the like manner as in Example. The results are shown in the following Table 3.

As will be understood from the results in Table 3, when the aluminum chloride catalyst is used, the proportion of m-benzyltoluene to the benzyltoluene mixture is almost the same as that of ZSM-5 catalyst, however, it is defective that ditolylmethane and heavier components are contained much in the reaction mixture.

COMPARATIVE EXAMPLE 3

A 250 ml reaction vessel was filled with 200 ml of Y-type zeolite of hydrogen type (made by Union Carbide & Carbon Corp., particle size: 12-14 mesh) and the catalyst was dried at 480° C. for 3 hours by a feed of dried nitrogen. A liquid mixture of 2 moles of toluene and 1 mole of diphenylmethane was fed to the reaction vessel at reaction temperature of 180° C., a pressure of 20 atm. (under nitrogen atmosphere) and LHSV of 1.0.

The effluent reaction mixture was analyzed by gas chromatography to determine the compositions after 20 hours' feed. The results are shown in the following Table 3.

According to this result, it was understood that the selectivity to m-benzyltoluene of Y-type zeolite is low and the lowering of catalytic activity is serious. This lowering of catalytic activity was not recovered even when the reaction temperature was raised from 180° C. to 250° C..

TABLE 1

(Liquid Composition in Example, wt %)

| Duration of Feed (hrs) | Benzene | Toluene | Xylene | Diphenyl-methane | m-Benzyl-toluene | o-Benzyl-toluene | p-Benzyl-toluene | Ditolyl-methane | Heavier Product |
|---|---|---|---|---|---|---|---|---|---|
| 20 | 18.9 | 44.7 | 0.9 | 17.9 | 7.3 | 0.5 | 5.1 | 3.6 | 1.0 |
| 80 | 14.6 | 32.6 | 0.4 | 24.1 | 12.0 | 0.9 | 7.8 | 5.8 | 1.8 |
| 120 | 13.2 | 29.9 | 0.5 | 24.9 | 13.9 | 1.0 | 8.6 | 6.3 | 1.7 |
| 160 | 13.2 | 29.3 | 0.4 | 26.9 | 12.6 | 0.8 | 8.6 | 7.0 | 1.2 |
| 200 | 13.2 | 34.0 | 0.4 | 27.8 | 9.8 | 0.4 | 7.6 | 5.7 | 1.1 |
| 300 | 13.1 | 34.4 | 0.5 | 27.8 | 10.0 | 0.5 | 7.8 | 4.8 | 1.1 |
| 500 | 13.0 | 33.8 | 0.5 | 28.7 | 9.7 | 0.3 | 8.7 | 4.7 | 0.6 |
| 800 | 13.1 | 34.6 | 0.4 | 29.2 | 9.0 | 0.2 | 8.0 | 5.0 | 0.5 |

TABLE 2

(Liquid Composition in Comparative Example 1, wt. %)

| Duration of Feed (hrs) | Benzene, Toluene, & Xylene | Diphenyl-methane | m-Benzyl-toluene | o-Benzyl-toluene | p-Benzyl-toluene | Ditolyl-methane | Heavier Product |
|---|---|---|---|---|---|---|---|
| 20 | 56.9 | 22.5 | 5.0 | 1.8 | 3.0 | 2.6 | 8.2 |
| 80 | 56.6 | 24.7 | 4.3 | 1.7 | 2.9 | 2.5 | 7.3 |
| 120 | 56.2 | 24.9 | 4.3 | 1.7 | 2.9 | 2.4 | 7.6 |
| 160 | 55.9 | 25.0 | 4.2 | 1.8 | 2.7 | 2.3 | 8.1 |
| 200 | 55.4 | 25.3 | 4.2 | 1.8 | 3.0 | 2.4 | 7.9 |
| 300 | 56.2 | 25.1 | 3.8 | 1.7 | 2.9 | 2.4 | 7.9 |
| 500 | 55.8 | 26.0 | 3.6 | 1.6 | 2.6 | 2.2 | 8.2 |
| 800 | 47.2 | 37.8 | 3.2 | 1.6 | 2.6 | 2.1 | 5.5 |

TABLE 3

(Liquid Composition in Comparative Examples 2 & 3, wt. %)

| Example | Duration of Feed (hrs) | Benzene, Toluene, & Xylene | Diphenyl-methane | m-Benzyl-toluene | o-Benzyl-toluene | p-Benzyl-toluene | Ditolyl-methane | Heavier Product |
|---|---|---|---|---|---|---|---|---|
| Comp. Exam. 2 | 5 | 62.8 | 6.9 | 8.4 | 1.3 | 3.3 | 6.4 | 10.9 |
| Comp. Exam. 3 | 20 | 52.2 | 44.9 | 1.1 | 0.4 | 0.5 | 0.4 | 0.5 |

What is claimed is:

1. A method for producing m-benzyltoluene which is characterized in that toluene and diphenylmethane are allowed to react at a reaction temperature in the range of 170 to 400° C. in the presence of a crystalline synthetic zeolite catalyst in which the molar ratio of $SiO_2/Al_2O_3$ is 20 or higher and the openings of main pores are formed by ten-membered oxygen rings.

2. The method for producing m-benzyltoluene in claim 1, wherein said crystalline synthetic zeolite catalyst is ZSM-5 type catalyst.

3. The method for producing m-benzyltoluene in claim 2, wherein said ZSM-5 type catalyst is ZSM-5.

4. The method for producing m-benzyltoluene in claim 1, wherein said molar ratio of toluene to diphenylmethane to be fed into the reaction system is in the range of 0.5 to 20.

5. The method for producing m-benzyltoluene in claim 1, wherein said reaction temperature is in the range of 200 to 350° C..

* * * * *

UNITED STATES PATENT AND TRADEMARK OFFICE
CERTIFICATE OF CORRECTION

PATENT NO.   : 4,899,009
DATED        : February 6, 1990
INVENTOR(S)  : Shigenobu Kawakami, Keji Endo, Hideyuki Dohi and Atsushi Sato It is certified that error appears in the above-identified patent and that said Letters Patent is hereby corrected as shown below:

On the title page, item [54], the title of the invention should read:
--METHOD FOR PRODUCING M-BENZYLTOLUENE--

Signed and Sealed this

Eleventh Day of December, 1990

*Attest:*

HARRY F. MANBECK, JR.

*Attesting Officer*  *Commissioner of Patents and Trademarks*